(12) United States Patent
Harvey (10) Patent No.: US 10,000,433 B1
(45) Date of Patent: Jun. 19, 2018

(54) BISPHENOLS AND HIGH-PERFORMANCE RESINS FROM TERPENES

(71) Applicant: The United States of America as represented by the Secretary of the Navy, Washington, DC (US)

(72) Inventor: Benjamin G. Harvey, Ridgecrest, CA (US)

(73) Assignee: The United States of America as Represented by the Secretary of the Navy, Washington, DC (US)

( * ) Notice: Subject to any disclaimer, the term of this patent is extended or adjusted under 35 U.S.C. 154(b) by 0 days. days.

(21) Appl. No.: 15/277,506

(22) Filed: Sep. 27, 2016

(51) Int. Cl.
| | |
|---|---|
| *C07C 39/16* | (2006.01) |
| *C08G 64/06* | (2006.01) |
| *C07C 261/02* | (2006.01) |
| *C07D 303/30* | (2006.01) |
| *C07C 37/60* | (2006.01) |
| *C07C 37/11* | (2006.01) |

(52) U.S. Cl.
CPC .............. *C07C 39/16* (2013.01); *C07C 37/11* (2013.01); *C07C 37/60* (2013.01); *C07C 261/02* (2013.01); *C07D 303/30* (2013.01); *C08G 64/06* (2013.01)

(58) Field of Classification Search
CPC ............................ C09J 193/04; C08L 2666/06
USPC ......... 252/48.2; 568/718; 528/176, 196, 198
See application file for complete search history.

(56) References Cited

U.S. PATENT DOCUMENTS 5,236,608 A * 8/1993 Martella ................ C08G 75/14
44/435

\* cited by examiner

*Primary Examiner* — Terressa Boykin
(74) *Attorney, Agent, or Firm* — Stuart H. Nissim (57) ABSTRACT

The invention describes a high yield process that utilizes selective catalysts for the conversion of abundant, naturally occurring terpenes into bisphenols, and their derivative bis(cyanate)esters, resins, and polymers. High performance, low-cost composite materials with low moisture uptake and high glass transition temperatures suitable for aerospace applications can be prepared from these renewable starting materials.

20 Claims, 6 Drawing Sheets

BISPHENOLS AND HIGH-PERFORMANCE RESINS FROM TERPENES

STATEMENT REGARDING FEDERALLY SPONSORED RESEARCH OR DEVELOPMENT

The invention described herein may be manufactured and used by or for the government of the United States of America for governmental purposes without the payment of any royalties thereon or therefor.

BACKGROUND OF THE INVENTION

As the world population continues to increase, more pressure is exerted on the availability of natural resources, including petroleum. Sustainable feedstocks are becoming more important and the functionality of these feedstocks provides both challenges and opportunities. Polymers account for approximately 7% of total petroleum use and thus represent important targets for sustainable chemistry. Over the last several years a number of researchers have investigated the conversion of renewable phenols from lignin and other biomass sources to bisphenols and derivative polymers. These renewable bisphenols can be converted to a wide variety of resins including polycarbonates and epoxy resins.

Cyclic terpenes are another important source of renewable phenols. Although not as abundant as lignin, naturally occurring terpenoids, including p-cymene, α- and β-pinene, are readily available in the form of turpentine. Approximately 350,000 tons of turpentine are produced annually with most of it generated as a byproduct of paper production. Limonene is another important terpene which is found in the skins of citrus fruit. Approximately 77 million kg of limonene are generated annually, primarily as a byproduct of orange juice production. In addition to isolation from trees and other organic matter, terpenoids are readily accessible via biosynthetic routes in which metabolically engineered organisms produce the molecules from sugar substrates. Utilization of lignocellulosic sugars and implementation of this approach on an industrial scale could legitimately allow for terpenoids to supplant various petroleum-based polymer feedstocks.

Figure 1:
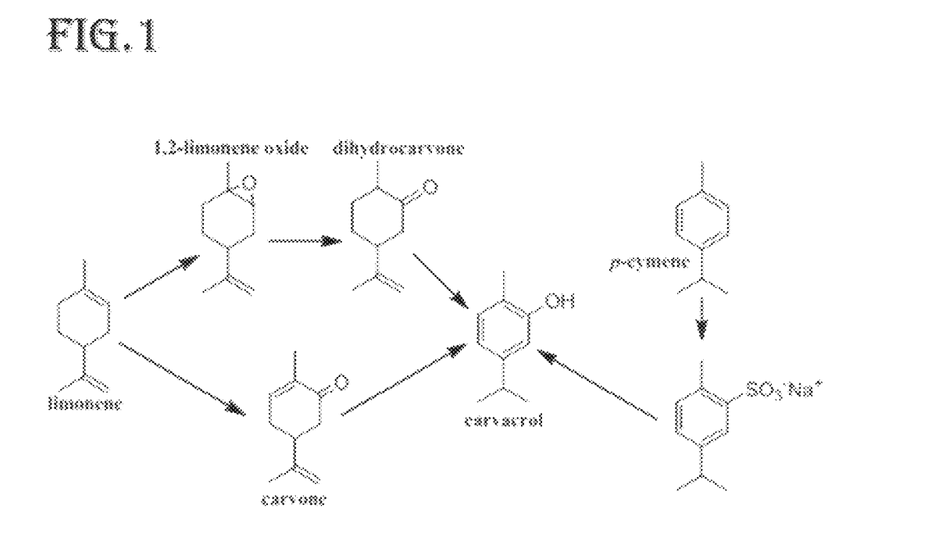
FIG. 1 is an illustration of synthetic pathways for preparing carvacrol, according to embodiments of the invention.
Figure 2:
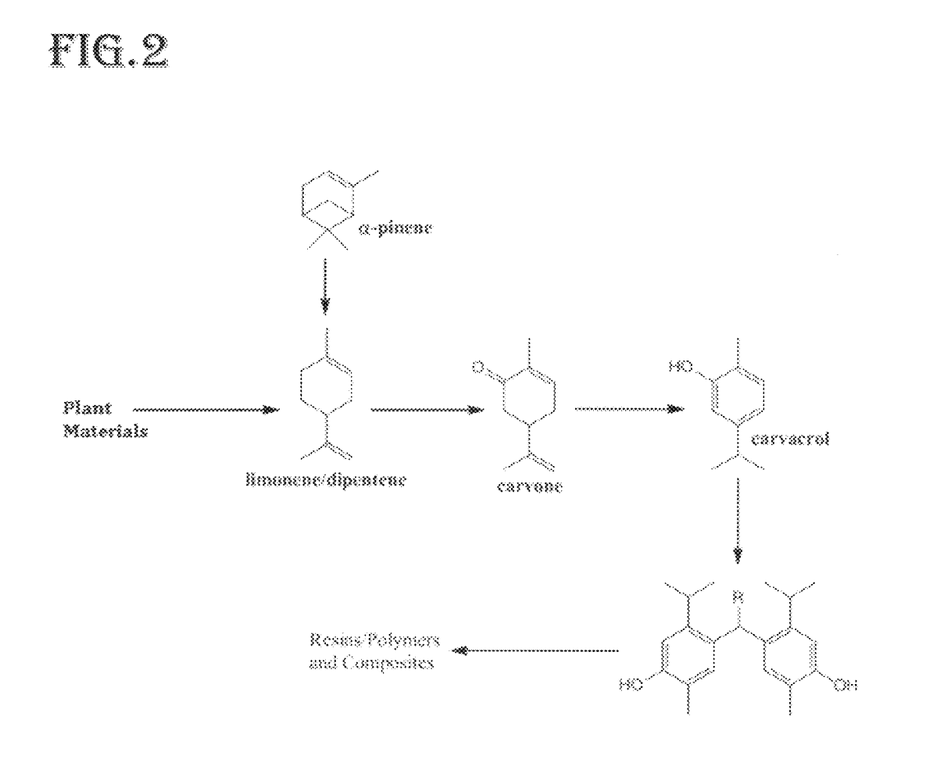
FIG. 2 is an illustration of synthetic pathways for conversion of terpenes to bisphenols and polymers, according to embodiments of the invention.

Terpenes are incredibly versatile molecules for the generation of polymers. The reactive double bonds of terpenes such as β-pinene allow for direct polymerization, while aromatic molecules such as p-cymene can be accessed via dehydrogenation. Similarly, phenolic terpenoids such as carvacrol and thymol can be readily generated from terpenes by selective oxidation and isomerization reactions. Carvacrol is a component of the essential oils of thyme and oregano and has previously been synthesized by a number of routes starting from various terpenoids (FIG. 1). One of the early routes involved reaction of p-cymene with concentrated sulfuric acid to generate the sulfonic acid salt. This salt was then fused with sodium hydroxide to generate carvacrol. Another route could start by oxidation of limonene to carvone followed by isomerization to carvacrol with sulfated zirconia. The classic route to carvone uses NOCl as the oxidizing agent, but more recently, highly selective oxidation of limonene to carvone has been accomplished using a Cr-based MOF catalyst and tert-butyl hydrogen peroxide as the oxidant. Limonene can also be selectively oxidized to 1,2-limonene oxide which is readily isomerized to dihydrocarvone. Dihydrocarvone can then be oxidized to carvacrol with reagents including ferric chloride.

The present invention provides novel bisphenols and novel methods for producing bisphenols and their products from renewable feedstocks In addition to the issue of finding renewable sources for resins, there are problems with resins when exposed to water. This is a major problem for resins used in naval ships, vehicles, and structures. This arises because water interactions with epoxy resins, for example, can degrade the mechanical properties of the resins. Water can cause the resins to swell and to produce what is called "crazing" of the surfaces. Water absorbed in the resins can reduce the glass transition temperature (Tg) of the polymers and make them weaker. When polymers are utilized in composite materials, high water uptake coupled with rapid heating can lead to delamination of composite panels and parts. For example, in high performance aircraft, where surface operating temperatures (particularly the leading edges) can reach well above 100° C. at high speeds, conventional epoxy resins no longer offer adequate performance.

Resins and polymers made using the bisphenols of the present invention and their derivatives address this issue by exhibiting both low water uptake and high $T_g$.

It is to be understood that the foregoing general description and the following detailed description are exemplary and explanatory only and are not to be viewed as being restrictive of the invention, as claimed. Further advantages of this invention will be apparent after a review of the following detailed description of the disclosed embodiments, which are illustrated schematically in the accompanying drawings and in the appended claims.

DETAILED DESCRIPTION OF THE EMBODIMENTS OF THE INVENTION

Embodiments of the invention generally relate to the facile, high yield synthesis of bisphenols by acid catalyzed coupling of carvacrol with an aldehyde or a ketone. These novel syntheses exhibit higher yield than previously available. Embodiments also include the further conversion of synthesized bisphenols to bis(cyanate)esters.

Embodiments also include the synthesis of both thermosetting resins and thermoplastic polycarbonates derived from the bisphenols. In addition to the benefits of utilizing a renewable source, the thermosetting resins and thermoplastic polycarbonates of the present invention have superior characteristics compared to those of conventional resins.

Compounds encompassed by the present invention are represented by the formula:

where R and R' are independently H, an alkyl group of up to about 10 carbon atoms, an aromatic group, an alkyl aromatic group, fluorine, fluorinated alkane, chlorine, or chlorinated alkane;

R" is H, CN, a glycidyl group, or a phthalonitrile group; and,

R''' is an alkyl of 1 to 20 carbons.

In further embodiments, the bisphenols are converted to bis(cyanate)esters, thermosetting resins and polymers by techniques known in the art. Examples of thermosetting resins include, but are not limited to, cyanate esters, epoxies, phthalonitriles, and benzoxazines. Examples of representative polymers include, but are not limited to, polycarbonates, polysulfones, polyesters, polyesterstyrenes, alkylphenolics and polyalylates. These materials can be utilized by themselves, blended with other resins and polymers, or combined with support materials for the fabrication of composites Embodiments of the synthetic process comprise:
  obtaining a terpene;
  oxidizing the terpene to generate an alpha,beta-enone;
  isomerizing the enone to a phenol; and,
  reacting the phenol with an aldehyde or ketone to generate a bisphenol.

Another embodiment of the synthetic process comprises:
  obtaining a terpene;
  oxidizing the terpene to generate an 1,2-epoxide;
  isomerizing the 1,2-epoxide to a ketone;
  oxidizing the ketone to a phenol; and,
  reacting the phenol with an aldehyde or ketone to generate a bisphenol.

The bisphenol can be further processed to produce bis (cyanate)esters. The bisphenol can be converted to resins and polymers by conventional methods.

One preferred terpene is limonene (dipentene) which is an abundant hydrocarbon present in orange peels and produced by a variety of plants. The invention describes a process for the conversion of limonene into carvacrol through a two-step procedure. This process utilizes heterogeneous catalysts and environmentally friendly oxidants to selectively produce carvacrol which can then be condensed with aldehydes or ketones to generate bisphenols. The properties of the bisphenols can be tuned by changing the aldehyde or ketone group. These bisphenols can serve as precursors to a variety of resins and polymers including, but not limited to cyanate ester resins, epoxy resins, polyesters, polycarbonates, polysulfones, polyester-styrenes, alkylphenolics, and polyalylates. The substitution of the aromatic ring of carvacrol results in high yields and selective formation of para-bisphenols. Resins and thermoplastics derived from these bisphenols have low water uptake due to the presence of aliphatic groups on the aromatic ring. These resins and thermoplastics exhibit preferred low water uptake less than 10%, more preferably less than about 1%.

Preferred sources for limonene are renewable; such sources include, for example, isolating limonene directly from a renewable source (such as citrus peels); generating limonene by the Diels-Alder cyclodimerization of isoprene; or isomerizing a crude turpentine feedstock or alpha-pinene to limonene.

In one preferred method, limonene is isolated from orange peels or other plant materials by steam distillation or solvent extraction.

In another preferred method, limonene is isolated by the fractional distillation of mixed terpene feedstocks or essential oils. In yet another preferred embodiment, limonene is obtained from fermentation of sugar or biomass sugars via a biosynthetic route.

In still other embodiments, limonene is generated by Diels-Alder cyclodimerization of isoprene.

In another embodiment, a crude turpentine feedstock or terpene mixture is isomerized to a mixture rich in limonene with a heterogeneous catalyst. Pure limonene is then isolated by fractional distillation.

In a preferred method, limonene is selectively oxidized to carvone with a heterogeneous catalyst and an oxidant. The catalyst can be based on a variety of transition metals, including high oxidation state V and Cr catalysts. Oxidants can include oxygen, hydrogen peroxide and i-butyl hydroperoxide among other reagents. In embodiments, the oxidant can be generated in situ as the reaction proceeds.

In a preferred method, carvone is isomerized to carvacrol using either a heterogeneous or homogenous catalyst. In preferred embodiments, catalysts can include sulfated zirconium or titanium oxide, zeolites, acid clays, cation exchange resins, and liquid acids including ionic liquids. Alkali catalysts can also be used for this transformation or the reaction can be performed via microwave radiation without a catalyst.

In preferred embodiments, carvacrol is allowed to react with an aldehyde or ketone in the presence of an acid catalyst to generate a bisphenol. Solid or liquid acid catalysts can be used for this reaction. The bisphenol is purified by techniques including washing, crystallization, sublimation, and column chromatography. The process of the current invention produces yields greater than 50%.

Examples of aldehydes include formaldehyde, acetaldehyde, propionaldehyde, butyraldehyde, isobutyraldehyde, vanillin, and other aromatic aldehydes. Examples of ketones include acetone, methylethylketone, 3-pentanone, 2-pentanone, and the like.

Although embodiments of the invention are described in considerable detail, including references to certain versions thereof, other versions are possible. Therefore, the spirit and scope of the appended claims should not be limited to the description of versions included herein.

EXAMPLES

The following examples are for illustration purposes only and not to be used to limit any of the embodiments.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

For the following examples, all reagents were purchased from Aldrich and used as received except for triethylamine which was distilled from sodium benzophenone under nitrogen. NMR spectra were collected with a Bruker Avance II 300 MHz NMR spectrometer. $^1$H and $^{13}$C NMR chemical shifts are reported versus the deuterated solvent peak [CDCl$_3$: δ 7.27 ppm ($^1$H), 77.23 ppm ($^{13}$C)]. FTIR spectra were collected on a Thermo Nicolet Nexus 870 FTIR. The FTIR spectra are an average of 32 scans at 4 cm$^{-1}$ resolution. Elemental analysis was performed by Atlantic Microlabs Inc. Norcross, Ga.

Example 1

Synthesis of Carvacrol from Limonene

Limonene is oxidized to carvone with NOCl or with tert-butyl hydrogen peroxide in the presence of a catalyst. Carvone is then isomerized to carvacrol with an acid catalyst (e.g. sulfated zirconia)

Example 2

Limonene is oxidized to 1,2-limonene oxide which is then isomerized to dihydrocarvone with an acid catalyst (e.g. heteropoly acid). Dihydrocarvone is then allowed to react with an oxidizing agent (e.g. FeCl$_3$) to generate carvacrol.

Example 3

A methylene-bridged bisphenol was synthesized by reaction of carvacrol with 1,3,5-trioxane in dilute HCl at elevated temperature. The resulting bisphenol (4,4'-methylenebis(5-isopropyl-2-methylphenol)) precipitated as a solid block which allowed for separation from the reaction medium by simple decantation. The bisphenol was then purified by recrystallization from CH$_2$Cl$_2$. Only the para para-isomer was observed suggesting that the steric hindrance of the alkyl groups plays a significant role in directing the formaldehyde coupling.

Example 4

Synthesis of 4,4'-methylenebis(5-isopropyl-2-methylphenol)

Carvacrol (10.00 g, 66.6 mmol) was combined with 1,3,5-trioxane (1.96 g, 21.8 mmol) and dispersed in water (60 mL). Concentrated HCl (15 mL) was added and the mixture was heated in an 80° C. oil bath for six hours. The product of the reaction consolidated into a solid off-white mass. The mixture was cooled to room temperature and the supernatant decanted. The solid product was dissolved in CH$_2$Cl$_2$ with mild heating and washed with water. The organic layer was dried over MgSO$_4$, concentrated under reduced pressure with mild heating, and placed in a −20° C. freezer overnight. The product crystallized as fine white needles which were collected by filtration, washed with cold hexanes, and dried under reduced pressure to yield 5.71 g (55%) of product. $^1$H NMR (CDCl$_3$) δ: 6.75 (s, 2H, Ph), 6.62 (s, 2H, Ph), 4.51 (bs, 2H, —OH), 3.86 (s, 2H, CH$_2$), 3.05 (sept, J=6.8 Hz, 2H, CH), 2.14 (s, 6H, Me), 1.18 (d, J=6.8 Hz, 12H, Me). Anal. Calcd for C$_{21}$H$_{28}$O$_2$: C, 80.73; H, 9.03. Found: C, 80.49; H, 9.02.

While 4,4'-methylenebis(5-isopropyl-2-methylphenol) has previously been prepared by reaction of carvacrol with formaldehyde under basic conditions, the reported yield of 4,4'-methylenebis(5-isopropyl-2-methylphenol) was only 10%. Under the method of the present invention, high purity yields of at least 55% were obtained without optimization.

Example 5

Synthesis of bis(4-cyanato-2-isopropyl-5-methylphenyl)methane (CarvCy)

A round-bottomed flask equipped with a magnetic stirbar was charged with 4,4'-methylenebis(5-isopropyl-2-methylphenol) (650 mg, 2.0 mmol) and acetone (20 mL). The mixture was stirred until the solids dissolved. The flask was then cooled in a dry ice/acetone bath and CNBr (657 mg, 6.2 mmol) was added. Triethylamine (440 mg, 4.4 mmol, 2.2 equiv) was then added dropwise over 3 min. White solids precipitated after the addition. The cooling bath was removed and the mixture was stirred at ambient temperature for 1.5 hours. The mixture was partitioned between Et$_2$O (50 mL) and H$_2$O (50 mL). The organic phase was further washed with H$_2$O (50 mL) followed by brine (50 mL). Next, the organic phase was dried over anhydrous MgSO$_4$ and the solvent was removed under reduced pressure leaving the product as a white crystalline solid (690 mg, 91%). $^1$H NMR (CDCl$_3$) δ: 735 (s, 2H, Ph), 6.69 (s, 2H, Ph), 3.97 (s, 2H, CH$_2$), 3.06 (sept, J=6.8 Hz, 2H, CH), 220 (s, 6H, CH$_3$), 1.22 (d, J=6.8 Hz, 12H, CH$_3$). $^{13}$C NMR (CDCl$_3$) δ: 150.8, 147.4, 135.5, 133.2, 123.5, 111.8, 109.5, 33.9, 29.3, 23.5, 15.0. Anal. Calcd for C$_{23}$H$_{26}$N$_{22}$: C, 76.21; H, 7.23; N, 7.73. Found: C, 76.05; H, 7.25; N, 7.75.

Example 6

Figure 9:
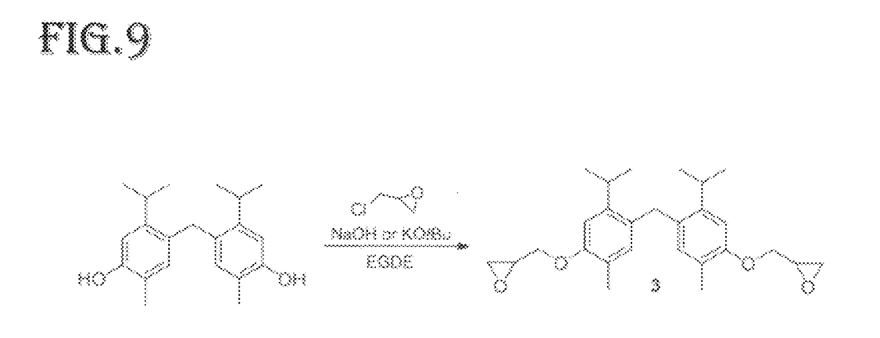
FIG. 9 is an illustration of synthetic pathways for the preparation of an epoxy monomer, according to embodiments of the invention.

Synthesis of bis(2-isopropyl-5-methyl-4-(oxiran-2-ylmethoxy)phenyl)methane (3-FIG. 9)

To a solution of potassium tert-butoxide (4.5 g, 40 mmol) in ethylene glycol dimethyl ether (EGDE, 25 mL) cooled to 0° C., a solution of 4,4'-methylenebis(5-isopropyl-2-methylphenol) (5.0 g, 16 mmol) in EGDE (50 mL) was added dropwise. The solution turned light green. Epichlorohydrin (14.8 g, 160 mmol) was added to the stirred solution, which was allowed to warm to room temperature and then heated to 70° C. for 4 h. A white solid began precipitating after one h. Diethyl ether (100 mL) was added to dilute the reaction mixture, which was then washed with 2×100 mL deionized water and 100 mL of brine. The organic fraction was dried over MgSO4, and the volatiles were removed at 100° C. under reduced pressure (5 torr) to yield the product as a white powder upon cooling (5.24 g, 77.2%). mp=92-95° C. 1H NMR (CDCl3) δ: 6.80 (s, 2H, Ph), 6.66 (s, 2H, Ph), 4.26 (dd, J=11.0 Hz, 3.3 Hz, 2H, CH2), 4.04 (dd, J=11.0 Hz, 5.4 Hz, 2H, CH2), 3.90 (s, 2H, CH2), 3.44-3.39 (m, 2H, CH), 3.11 (sept, J=6.8 Hz, 2H, CH), 2.94 (dd, J=5.0 Hz, 4.2 Hz, 2H, CH2), 2.82 (dd, J=5.0 Hz, 2.7 Hz, 2H, CH2), 2.16 (s, 6H, CH3), 1.22 (d, J=6.8 Hz, 12H, CH3). 13C NMR (CDCl3) δ: 155.7, 145.7, 132.5, 130.3, 124.5, 109.1, 69.4, 50.8, 45.2, 34.0, 29.4, 24.13, 24.11, 16.1. Anal. Calcd for C27H36O4: C, 76.38; H, 8.55; O, 15.07. Found: C, 76.21; H, 8.60. GC/MS: major peak (95%) 424 (M+), minor peak (4%) 424 (M+), minor peak (1%) 206 (M+).

Example 7

Synthesis of bis(2-isopropyl-5-methyl-4-(oxiran-2-ylmethoxy)phenyl)methane 4,4'-methylenebis(5-isopropyl-2-methylphenol) (3.10 g, 10 mmol) was dissolved in a solution of EGDE (3.0 mL) and epichlorohydrin (8.0 mL). NaOH (1.00 g, 25 mmol) was added to the solution, which was heated to 70° C. for 4 h. The solution turned dark purple upon addition of the NaOH, and a white precipitate began to form within one h. Diethyl ether (50 mL) was added to dilute the reaction mixture, which was then washed with 2×50 mL deionized water and 50 mL of brine. The organic fraction was dried over MgSO4 and the volatiles were removed at 100° C. under reduced pressure (5 torr) to yield the product as a white powder upon cooling (3.52 g, 83.8%).

Example 8

X-ray Diffraction.

A specimen of CarvCy (Example 5), having approximate dimensions of 0.177 mm×0.225 mm×0.334 mm, was used for the X-ray crystallographic analysis. The X-ray intensity data were measured. A total of 1464 frames were collected. The total exposure time was 4.07 hours. The frames were integrated with the Bruker SAINT software package using a narrow-frame algorithm. The integration of the data using a monoclinic unit cell yielded a total of 35839 reflections to a maximum θ angle of 32.670 (0.66 Å resolution), of which 7077 were independent (average redundancy 5.064, completeness=99.4%, Rint=3.58%) and 5584 (78.90%) were greater than 2σ(F2). The final cell constants of a=9.0471(6) Å, b=17.5709(11) Å, c=12.9430(8) Å, β=109.2500(10)°, volume=1942.5(2) Å3, are based upon the refinement of the XYZ-centroids of 1461 reflections above 20 σ(I) with 4.674°<2θ<64.93°. Data were corrected for absorption effects using the multi-scan method (SADABS). The ratio of minimum to maximum apparent transmission was 0.956.

The final anisotropic full-matrix least-squares refinement on F2 with 250 variables converged at R1=4.95%, for the observed data and wR2=13.67% for all data. The goodness-of-fit was 1.035. The largest peak in the final difference electron density synthesis was 0.527 e-/Å3 and the largest hole was -0.280 e-/Å3 with an RMS deviation of 0.061 e-/Å3. On the basis of the final model, the calculated density was 1.239 g/cm3 and F(000), 776 e-. A cif file for CarvCy has been deposited with the Cambridge Structural Database (deposition number CCDC 1424051).

Example 9

Network Formation.

CarvCy (Example 5) was further purified by dissolution in dichloromethane, followed by passage through a W-Prep2XY Yamazen flash chromatography column, and removal of the solvent under reduced pressure. Purified CarvCy was then heated to approximately 135° C. and poured into a silicone rubber mold having a disc-shaped cavity and cured under flowing nitrogen at 150° C. for 1 h and 210° C. for 24 h using a ramp rate of 5° C./min, then cooled and de-molded. The resulting pale orange disc was 12 mm in diameter and 4 mm thick. The density of the disc was 1.06 g/mL.

Figure 3:
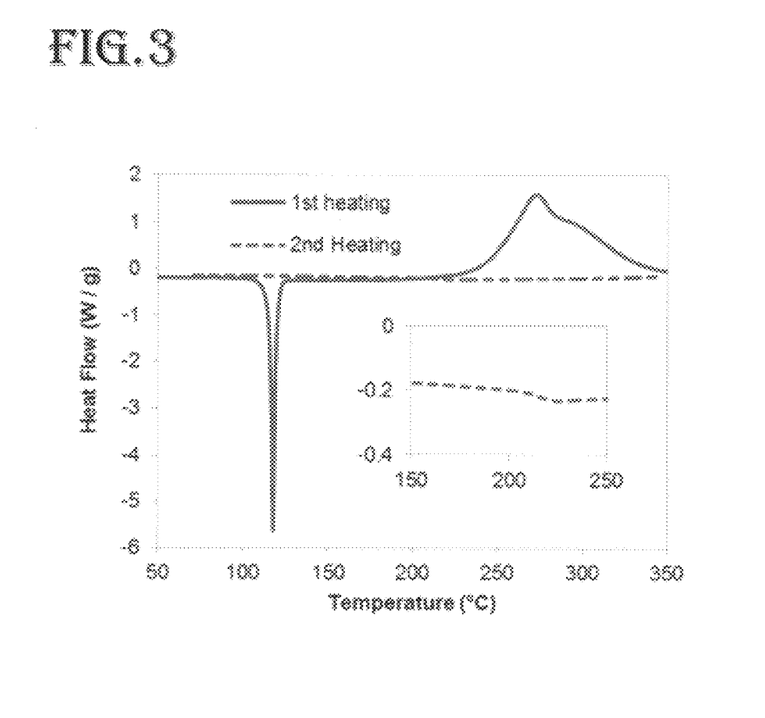
FIG. 3 is a graph showing DSC data for CarvCy, according to embodiments of the invention.

After characterizing the cyanate ester, the cure chemistry of the resin was first probed by DSC (FIG. 3). The resin melted cleanly at 117° C. with onset of cure observed at 194° C. The enthalpy change attributed to cyclotrimerization was 112 kJ/(mol —OCN), consistent with complete cure. The DSC curve obtained after cure of the resin indicates a conversion of about 97%.

Example 10

Network Characterization Techniques for CarvCy

For Differential Scanning Calorimetry (DSC), 5-10 mg pieces of the cured resin (Example 9) were hermetically sealed in aluminum DSC pans. Samples were then ramped under 50 mL/min of flowing nitrogen at 10° C./min, first heating to 350° C., cooling to 100° C., then re-heating to 350° C., using a TA Instruments Q200 differential scanning calorimeter.

Figure 4:
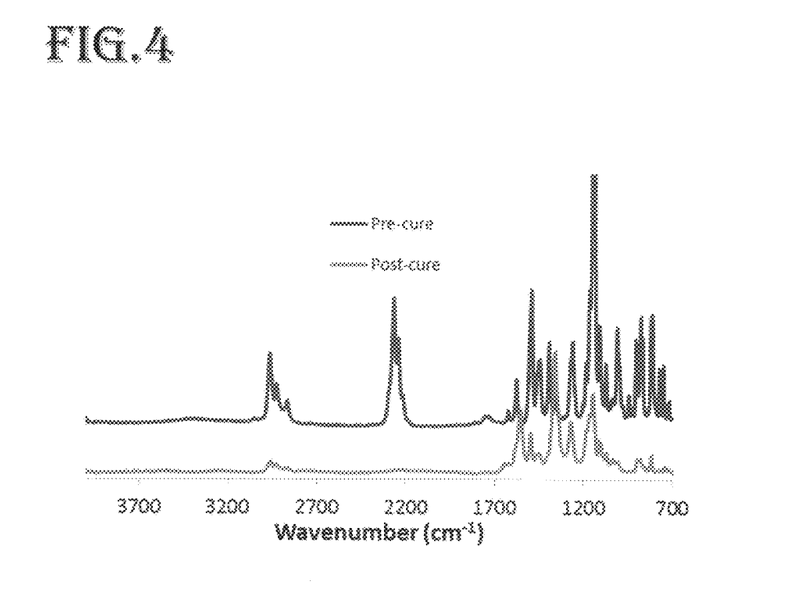
FIG. 4 is a graph showing FTIR data for CarvCy before and after cure, according to embodiments of the invention.

Similarly, IR spectra taken before and after the cure reaction showed complete elimination of the C—N stretching frequency, confirming the high degree of cure (FIG. 4).

Figure 5:
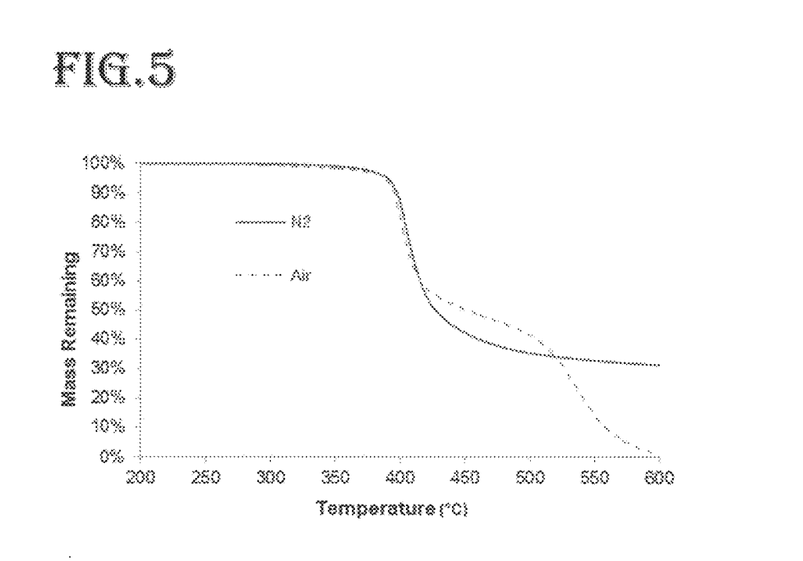
FIG. 5 is a graph showing TGA data for cured CarvCy, according to embodiments of the invention.

The thermal properties of the cured resin were then evaluated by TGA (FIG. 5). The material showed excellent thermal stability, particularly given the number of aliphatic groups present in the parent molecule. 5% weight loss was observed at 390 and 388° C. under $N_2$ and air, respectively. The char yield at 600° C. in nitrogen was 31%, while the char yield in air was less than 1%.

Example 11

Thermogravimetric Analysis (TGA).

Samples from Example 9 were heated to 600° C. at 10° C./min in a TA Instruments Q500 TGA under dry nitrogen or air flowing at 25 mL/min, with the counterweight chamber purged with 10 mL/min dry nitrogen.

Figure 6:
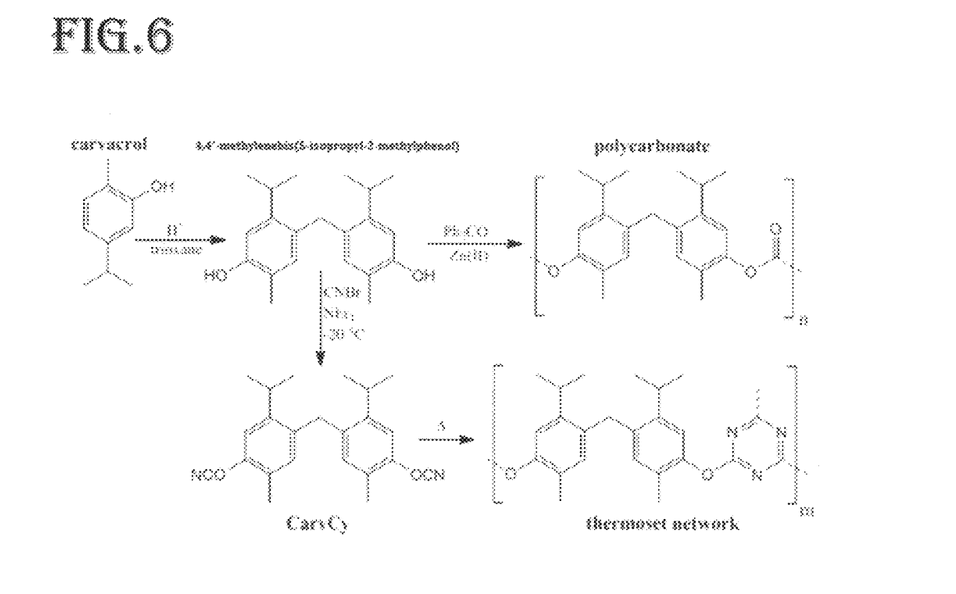
FIG. 6 is an illustration of synthetic pathways for the preparation of a cyanate ester and polycarbonate from carvacrol, according to embodiments of the invention.
Figure 7:
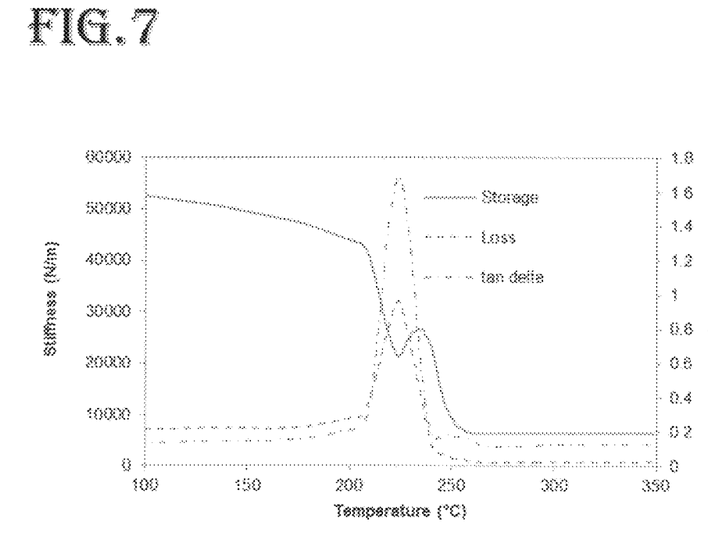
FIG. 7 is a graph showing TMA data for cured CarvCy, according to embodiments of the invention.

The Tg of the cured resin was obtained via thermomechanical analysis (FIG. 6) and determined to be 224° C. (loss peak).

Example 12

Oscillatory Thermomechanical Analysis (OTMA).

Cured discs (Example 9) were tested via OTMA with a TA Instruments Q400 series analyzer under 50 mL/min of nitrogen flow. The discs were initially held in place with a compressive force of 0.2 N using the standard ~5 mm diameter flat cylindrical probe. The force was then modulated at 0.05 Hz over an amplitude of 0.1 N (with a mean force of 0.1 N) and the temperature was ramped twice (heating and cooling) between -50° C. and 200° C. (to aid in determination of thermal lag) followed by heating to 350° C., cooling to 100° C., and re-heating to 350° C., all at 50° C./min. For samples previously exposed to hot water, the heating rate was decreased to 20° C./min and the order of segments was: heating to 350° C., cooling to 100° C., two cycles between 100° C. and 200° C. for thermal lag determination, and finally heating to 350° C.

Example 14

To evaluate the performance of the resin under hot/wet conditions, a cured resin sample (Example 9) was placed in 85° C. water for 4 days and exhibited water uptake of only 0.7%. This is one of the lowest water uptakes measured for any cyanate ester when compared to other cyanate esters, such as RTX-366 (0.6-0.7%):

RTX-366 and a cyanate ester prepared from bisphenol T [PFCBCy, 0.56 (10)%]:

PFCBCy

RTX-366 has a fully cured $T_g$ (uncatalyzed) of 204° C. while PFCBCy has a fully cured $T_g$ of 190° C. By comparison, CarvCy:

CarvCy has a $T_g$ 20-35° C. higher and outperforms both of these other resins when water uptake and glass transition temperature are considered in concert.

Example 15

To further evaluate the behavior of CarvCy in humid environments, a wet $T_g$ was determined using a resin disk subjected to the hot water treatment. The wet $T_g$ of CarvCy (221° C.) was only three degrees lower than the dry $T_g$, showing that the cured resin was virtually unaffected by the water exposure at elevated temperature. It was shown that having an alkyl group ortho to the cyanate ester group can lead to decreased water uptake. Similarly, the combination of the ortho-alkyl groups and the hydrophobic isopropyl groups result in the excellent resistance of this material to water.

Example 16

Water Immersion Testing.
Cured discs of polymers prepared in Example 9 were dried to a±0.0001 g constant weight in a vacuum dessicator, then weighed and immersed in approximately 250 mL deionized water maintained at 85° C. for 96 hours. After removal from the water, samples were patted dry and weighed to determine the moisture uptake (on a dry weight basis). These samples were used for wet $T_g$ determinations.

Example 17

Figure 8:
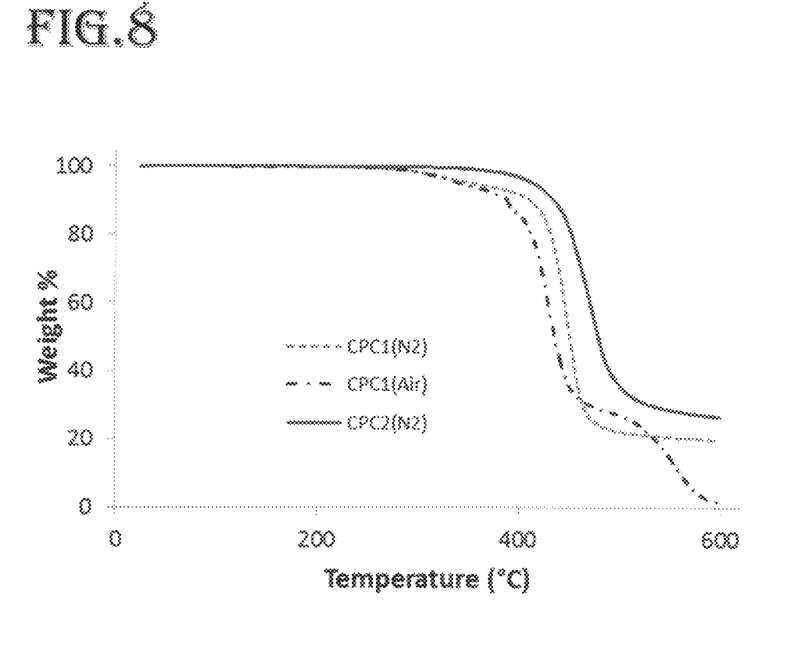
FIG. 8 is a graph showing TGA data for carvacrol derived polycarbonates in air and nitrogen, according to embodiments of the invention.

Synthesis of a Polycarbonate from the Bisphenol.
Reaction of 4,4'-methylenebis(5-isopropyl-2-methylphenol) with diphenyl carbonate in the presence of zinc acetate resulted in a $CH_2Cl_2$ soluble polycarbonate (CPC1) with $M_n$=5519 daltons and $M_w/M_n$=3.06. The polymer was then analyzed via DSC and a glass transition temperature of 113° C. was observed. This value is about 15° C. lower than that of a bisphenol-A derived polycarbonate of similar molecular weight. TGA showed 5% weight loss at 353° C. under nitrogen and 342° C. in air (FIG. 8). The char yield was 19.8% under nitrogen and only 1.5% in air. These results are similar to those observed for CarvCy, while the char yield in nitrogen is about 10% less than that observed for bisphenol A polycarbonate. No melting point was observed in the DSC up to 250° C.

Example 18

Polycarbonate Synthesis (CPC1).
4,4'-methylenebis(5-isopropyl-2-methylphenol) (Example 4) (0.50 g, 1.6 mmol), diphenyl carbonate (0.36 g, 1.7 mmol) and $Zn(Ac)_2·2H_2O$ (9.7 mg, 0.0442 mmol) were combined in a flask. The mixture was heated to 190° C. under $N_2$ and held at that temperature for 4 hours. The pressure in the flask was then reduced to approximately 10 torr and the temperature was maintained for an additional 2 hours. The pressure was then reduced to 1 Torr for 16 hours. The flask was cooled to room temperature and the resulting yellow, resinous solid was dissolved in $CH_2Cl_2$, filtered through a 0.2 µm syringe filter, and concentrated to approximately 5 mL. The product was then precipitated in methanol, collected on a glass frit, and dried in a vacuum oven overnight. $^1H$ NMR ($CDCl_3$) δ: 7.15 (s, 2H, Ph), 6.75 (s, 2H, Ph), 3.98 (bs, 2H, $CH_2$), 3.07 (sept, J=6.8 Hz, 2H, CH), 221 (s, 6H, Me), 1.22 (d, J=6.8 Hz, 12H, Me). $^{13}C$ NMR ($CDCl_3$) δ: 152.1, 148.7, 146.3, 135.4, 132.6, 127.1, 118.4, 34.3, 31.1, 29.1, 23.8, 15.8.

Example 19

Polycarbonate Synthesis (Alternate Method, CPC2).
4,4'-methylenebis(5-isopropyl-2-methylphenol) (Example 4) (0.9370 g, 3 mmol) and triethylamine (47 µL, 0.3 mmol) were added to an aqueous NaOH solution (0.30 g, 7.5 mmol in 4 mL). A solution of triphosgene (0.367 g, 1.25 mmol) in $CH_2Cl_2$ (6 mL) was then added to the NaOH solution dropwise via syringe. The reaction mixture was vigorously stirred for 10 min and then transferred to a separatory funnel. The organic layer was washed 4 times with water and the organic layer was then poured into ca. 100 mL of rapidly stirring methanol. A white solid precipitated out and was collected on a Buchner funnel. The solid was then washed with methanol and water and dried on the filter for 30 min. The solid was further dried in a vacuum oven overnight to yield 0.69 g of white powder that was spectroscopically identical to CPC1.

Example 20

A higher molecular weight polycarbonate was then synthesized by interfacial polymerization with triphosgene.

This procedure resulted in a CH$_2$Cl$_2$ soluble polycarbonate (CPC2) with M$_n$=10,200 and M$_w$/M$_n$=1.60. The T$_g$ increased slightly to 119° C., approximately 20° C. lower than a BPA polycarbonate of equivalent molecular weight. The minor change observed in T$_g$ for CPC2 despite nearly doubling the molecular weight of CPC1 suggests that 120° C. is near the maximum T$_g$ for this class of polycarbonate. CPC2 exhibited higher thermal stability than CPC1 with 5% weight loss at 415° C. in nitrogen and a significantly higher char yield of 27%. This latter value is similar to that observed for BPA polycarbonate, a result that is somewhat surprising given the extra aliphatic groups present in CPC2.

Carvacrol and the derivative bisphenol 4,4'-methylenebis (5-isopropyl-2-methylphenol) are sustainable and versatile starting materials for the synthesis of both thermosetting and thermoplastic resins. The synthesis of carvacrol from abundant terpenoids and lignocellulosic sources allow for it to be produced on an industrially relevant scale. The bisphenol and the derivative bis(cyanate)ester can be readily utilized as a precursor to a variety of polymers including for example, but not limited to, cyanate ester resins, polycarbonates, epoxy resins, phthalonitrile resins, and polyether ether ketones. The unique functionality of carvacrol, as compared to simple phenols, allows for preferred properties—the aliphatic substituents greatly reduce the water uptake of the derived resins and polymers while maintaining a glass transition temperature and thermal stability that are superior to those of conventional petroleum-based resins.

While the invention has been described, disclosed, illustrated and shown in various terms of certain embodiments or modifications which it has presumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

The invention claimed is:

1. A para-substituted bisphenolic compound having the formula:

where R and R' are independently H, an alkyl group of up to about 10 carbon atoms, an aromatic group, an alkyl aromatic group, fluorine, fluorinated alkane, chlorine, or chlorinated alkane;
where R'' is H, CN, a glycidyl group, or a phthalonitrile group; and,
where R''' is an alkyl of 1 to 20 carbons.

2. The compound of claim 1 having the formula:

3. The compound of claim 1 having the formula:

4. The compound of claim 1 having the formula:

5. A process for converting terpene feedstock to para-substituted bisphenolic compounds having the formula where R and R' are independently H, an alkyl group of up to about 10 carbon atoms, an aromatic group, an alkyl aromatic group, fluorine, fluorinated alkane, chlorine, or chlorinated alkane;
where R'' is H, CN, a glycidyl group, or a phthalonitrile group; and,
where R''' is an alkyl of 1 to 20 carbons, comprising:
converting a monocyclic terpene to a phenol;
wherein said phenol has the formula:

where R''' is an alkyl of 1 to 20 carbons and,
reacting said phenol with an aldehyde or ketone to generate said para-substituted bisphenolic compound,
wherein said aldehyde or ketone has the formula:

where R and R' are independently H, an alkyl group of up to about 10 carbon atoms, an aromatic group, an alkyl aromatic group, fluorine, fluorinated alkane, chlorine, or chlorinated alkane.

6. The process of claim 5 comprising:
oxidizing said monocyclic terpene to generate an alpha, beta-enone;
isomerizing said enone to a phenol;
wherein said phenol has the formula:

where R''' is an alkyl of 1 to 20 carbons
and,
reacting said phenol with an aldehyde or ketone to generate said para-substituted bisphenolic compound,
wherein said aldehyde or ketone has the formula:

where R and R' are independently H, an alkyl group of up to about 10 carbon atoms, an aromatic group, an alkyl aromatic group, fluorine, fluorinated alkane, chlorine, or chlorinated alkane.

7. The process of claim 5 comprising
oxidizing the monocyclic terpene to generate a 1,2-epoxide;
isomerizing the 1,2-epoxide to a ketone;
oxidizing the ketone to a phenol;
and,
wherein said phenol has the formula:

where R''' is an alkyl of 1 to 20 carbons
and,
reacting said phenol with an aldehyde or ketone to generate said para-substituted bisphenolic compound,
wherein said aldehyde or ketone has the formula:

where R and R' are independently H, an alkyl group of up to about 10 carbon atoms, an aromatic group, an alkyl aromatic group, fluorine, fluorinated alkane, chlorine, or chlorinated alkane.

8. The process of claim 5 wherein said monocyclic terpene is dipentene.

9. The process of claim 5 wherein said enone is carvone.

10. The process of claim 5 wherein said phenol is carvacrol.

11. The process of claim 5 wherein said aldehyde or ketone is selected from formaldehyde, paraformaldehyde, 1,3,5-trioxane, acetaldehyde, propionaldehyde, butyraldehyde iso-butyraldehyde, acetone, 2-butanone, 3-pentanone, 2-pentanone, or vanillin.

12. The process of claim 5 having a para-substituted bisphenolic compounds yield of greater than 50 percent by weight.

13. The process of claim 5 further comprising reacting said para-substituted bisphenolic compounds with a base and a cyanogen halide or cyanogen pseudohalide to produce a bis(cyanate) ester.

14. A polymer derived from the bisphenolic compounds of claim 1.

15. The polymer of claim 14 said polymer having a water uptake of less than about 1%.

16. The polymer of claim 14 said polymer comprising thermoset resins.

17. The polymer of claim 14, said polymer comprising thermoplastics.

18. The polymer of claim 14, said polymer comprising cyanate esters, epoxies, phthalonitriles, and benzoxazines, polycarbonates, polysulfones, polyesters, polyesterstyrenes, alkylphenolics, and polyalylates.

19. The polymer of claim 14, said polymer having a Tg greater than about 204° C.

20. The polymer of claim 14, said polymer having a Tg of about 224° C.

* * * * *